United States Patent
Deng

(10) Patent No.: US 9,301,872 B2
(45) Date of Patent: Apr. 5, 2016

(54) CONTACT LENS WEARING AND REMOVING CLIP

(71) Applicant: Syu-Guang Deng, New Taipei (TW)

(72) Inventor: Syu-Guang Deng, New Taipei (TW)

( * ) Notice: Subject to any disclaimer, the term of this patent is extended or adjusted under 35 U.S.C. 154(b) by 0 days.

(21) Appl. No.: 14/426,142

(22) PCT Filed: Aug. 23, 2013

(86) PCT No.: PCT/CN2013/082145
§ 371 (c)(1),
(2) Date: Mar. 4, 2015

(87) PCT Pub. No.: WO2014/036895
PCT Pub. Date: Mar. 13, 2014

(65) Prior Publication Data
US 2015/0216724 A1    Aug. 6, 2015

(30) Foreign Application Priority Data
Sep. 4, 2012 (CN) .......................... 2012 1 0323127

(51) Int. Cl.
*B25J 1/00* (2006.01)
*A61F 9/00* (2006.01)

(52) U.S. Cl.
CPC .................................... *A61F 9/0061* (2013.01)

(58) Field of Classification Search
USPC .......... 294/1.2, 1, 99.2, 902; D16/331; 606/1, 606/107, 210; 351/159.02
See application file for complete search history.

(56) References Cited

U.S. PATENT DOCUMENTS

| | | | | | |
|---|---|---|---|---|---|
| 528,257 | A | * | 10/1894 | Murray | 294/99.2 |
| 2,224,575 | A | * | 12/1940 | Montalvo-Guenard | 606/107 |
| 3,265,068 | A | * | 8/1966 | Holohan | 606/210 |
| 3,889,995 | A | * | 6/1975 | Lin | 294/99.2 |
| 4,245,859 | A | * | 1/1981 | Rainin | A61F 9/0061 294/1.2 |
| 4,479,672 | A | * | 10/1984 | Jermyn | 294/1.2 |
| 4,750,771 | A | * | 6/1988 | Emmett et al. | 294/99.2 |
| 4,964,663 | A | * | 10/1990 | Jermyn | 294/1.2 |
| 4,986,586 | A | * | 1/1991 | Eilrich et al. | 294/1.2 |
| 5,496,084 | A | * | 3/1996 | Miralles Medan | A61F 9/0061 294/1.2 |
| 2012/0191105 | A1 | * | 7/2012 | Deng | 606/107 |
| 2014/0159397 | A1 | * | 6/2014 | Saitoh et al. | 294/1.2 |

* cited by examiner

*Primary Examiner* — Paul T Chin
(74) *Attorney, Agent, or Firm* — Raymond Y. Chan; David and Raymond Patent Firm

(57) ABSTRACT

A contact lens tweezers includes two tips for gripping contact lens; and two thin rods that are extended from the bottom of two tips and connect to legs, which are used for supporting two tips, the two thin rods having high flexibility, bendable and hard to fracture. The two thin rods are bendable to enable the two tips to be more fit with the contact lens when used to remove the contact lens. The tips of this invention are provided with a convex structure to increase the friction area between the tips and contact lens, so that the contact lens gripping operation can be easily performed via the contact lens tweezers. And the bottom surfaces of the two tips and the convex structure of the contact lens tweezers form a curved structure, which prevents the eyes being pierced by the tips when removing the contact lens.

17 Claims, 5 Drawing Sheets

CONTACT LENS WEARING AND REMOVING CLIP

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

This invention relates to a structure of contact lens tweezers, especially about a contact lens wearing and removing structure.

2. Description of Related Arts

Due to technological development, many container products as contact lens cases which accommodate solution, which provide a clean and storage environment for contact lenses clean and preservation. For gripping contact lens, a lot of contact lens tweezers on the market, but the majority of contact lens tweezers do not use as a tool or removing contact lenses directly, which only provide contact lens removing function. Therefore, most people use fingers to wear and remove contact lenses from their eyeball. Because a lot of bacteria and dirt on finger, while wearing or removing contact lenses by hand, contact lens users likely to cause eye infections or feel discomfort of contact lens. Moreover, wearing or removing contact lens via fingers should note finger cleaning especially. And the fingers will be very close to eyes when wearing and removing contact lens, so that the wearer needs to trim fingernails regularly to avoid the fingernail injury the cornea. Wearing and removing contact lens is quite inconvenient for those people who have long fingernails or who like manicure. Therefore, the traditional wearing and removing method by finger should be improved.

Prior Taiwan published patent TW201034644 discloses a wearing device of contact lens hold the circumferential edge of the contact lens through several brackets which disposed at intervals, and then attach the contact lens to eyeball. But use the brackets to wear the contact lens maybe cause excessive force injury by the tips of the brackets, and the prior wearing device only for contact lens wearing and not for contact lens removing.

Prior China published patent CN201120235748.1 discloses a contact lens wearing tool which comprises a support head and the upper surface of the support head is concave for wearing the contact lens, but the contact lens wearing tool can't use to remove the contact lens.

Prior U.S. Pat. No. 4,245,859 discloses a tweezer device for manipulation of soft contact lenses. The end surface of the tweezer device comprises are slanted for wear or remove the contact lens. The friction force between the slanted surface and contact lens is low and the contact lens easy to drop and hard to wear or remove.

Prior U.S. Pat. No. 5,496,084 discloses a contact lens fitter-remover for wearing or removing contact lens which has a concavely curved cup-shaped surface of the free ends of legs, wherein a diametral notch in the concavity. But the concavely curved cup-shaped surface of the free ends of legs does not include a convex structure to increase the friction force between the contact lens and the remover, so as to hard to wear and remove the contact lens.

Above all the shortcomings of traditional contact lens tweezers, the inventor of the present invention discloses a novel contact lens wearing and removing tweezers to improve the aforementioned problems.

SUMMARY OF THE PRESENT INVENTION

An objective of the present invention is to provide a contact lens tweezers comprising two tips and a pair of legs, wherein each tip of the two tips comprises a bottom surface and a convex structure disposed on the bottom surface, when the two tips press close to each other, the bottom surface and the convex structure will form a curved structure, that increase the friction area between the tips and contact lens. Therefore, it is easier to remove the contact lenses from eye according to the shape of the eye, user can avoid scratching the eye when removal of contact lenses by finger, and prevent eye infection caused by the bacteria of finger.

Another objective of the present invention is to provide a contact lens tweezers comprising two tips and a pair of legs, wherein each tip of the two tips comprises a bottom surface and a convex structure disposed on the bottom surface, when the two tips press close to each other, the bottom surface and the convex structure will form a curved structure. Therefore, it is easy to catch the contact lens via the convex structure. It also can avoid scratching the eye when wearing of contact lenses by finger, and prevent eye infection caused by the bacteria of finger.

In order to achieve the said purposes, a contact lens tweezers comprising two tips for gripping contact lens; and a pair of legs for hand holding which each leg connects with the tip and the legs connect to each other; wherein the tip comprises a bottom surface and a convex structure disposed on the bottom surface, wherein when the two tips press close to each other, the bottom surface and the convex structure forming a curved structure for gripping or wearing contact lens.

As mentioned above the contact lens tweezers, which further comprising two thin rods, wherein each thin rod connects with the tip and the two thin rods are flexible, bendable and hard to fracture to enable the two tips to fit with the contact lens.

As mentioned above the contact lens tweezers, wherein when the two tips contact to each other, an angle formed between the two thin rods and the angle is between 15 and 90 degrees.

As mentioned above the contact lens tweezers, wherein the leg of the pair of legs further comprising a holding portion, the holding portion is for hand-held and apply force.

As mentioned above the contact lens tweezers, wherein the leg of the pair of legs further comprising a blocking lump, the blocking lump in the middle of the leg, when the blocking lumps of the pair of legs contact to each other, the two tips rotate according an rotation angle and forming a curved structure to prevent the two tips staggered if apply too much force when gripping or wearing the contact lens.

As mentioned above the contact lens tweezers, which the rotation angle is between 30 and 18 degrees.

As mentioned above the contact lens tweezers, which the material of the tip is silicone gel, polyethylene or Polyurethane.

As mentioned above the contact lens tweezers, which the bottom surface is triangular, rectangular, semicircular or polygonal.

As mentioned above the contact lens tweezers, wherein the convex structure is half-moon or semicircular. User can use the convex structure to attach the contact lens and remove the contact lens. The convex structure will increase the friction area between the tips and contact lens and it is easier to remove the contact lenses from eye according to the shape of the eye.

As mentioned above the contact lens tweezers, wherein the materials of the pair of legs and two thin rods are flexible material, such as plastic, rubber or metal. The two thin rods are highly flexible, bendable and hard to fracture which allow the two tips attach to the contact lens well.

As mentioned above the contact lens tweezers, which the two thin rods is cylinder or cuboid.

As mentioned above the contact lens tweezers, which the shape of the pair of legs is U-shape or V-shape.

As mentioned above the contact lens tweezers, wherein the shape of the curved structure is spoon-shaped, bowl-shaped or semicircular, so the contact lens is easy to put on the curved structure.

Please refer to the following description and accompanying drawings to understand the characteristics and advantages of the present invention.

DETAILED DESCRIPTION OF THE PREFERRED EMBODIMENT

Figure 1:
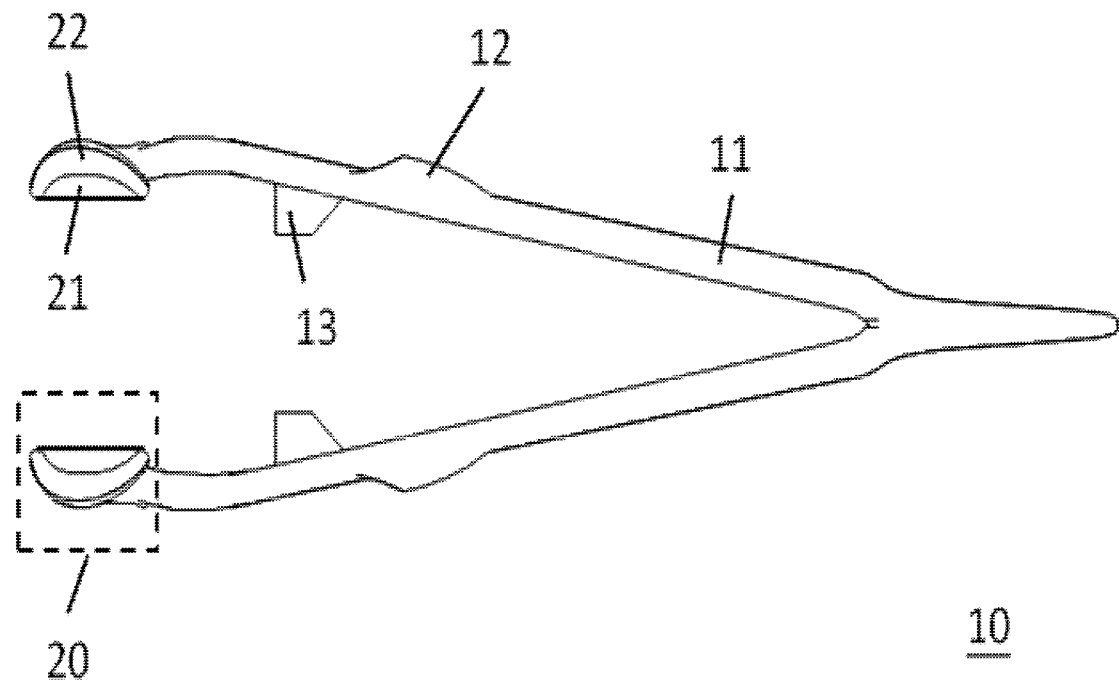
FIG. 1 is a top view of the contact lens tweezers in accordance with the first embodiment.

In order to make a person skilled in the art can understand and well known this invention, detail description, drawings and reference characters of the embodiments of the present invention are disclosed, but is not limited thereto.

Referring to FIG. 1, a top view of the contact lens tweezers in accordance with the first embodiment is shown. A contact lens tweezers 10 comprises tips 20, a pair of legs 11, holding portion 12 and blocking lump 13. The tips 20 are for gripping contact lens. The pair of legs 11 connects with the tips and the legs connect to each other to form a V-shape appearance. The material of the pair of legs 11 is flexible material like plastic and the pair of legs 11 is for hand holding and apply enforce to grip contact lens.

Figure 2:
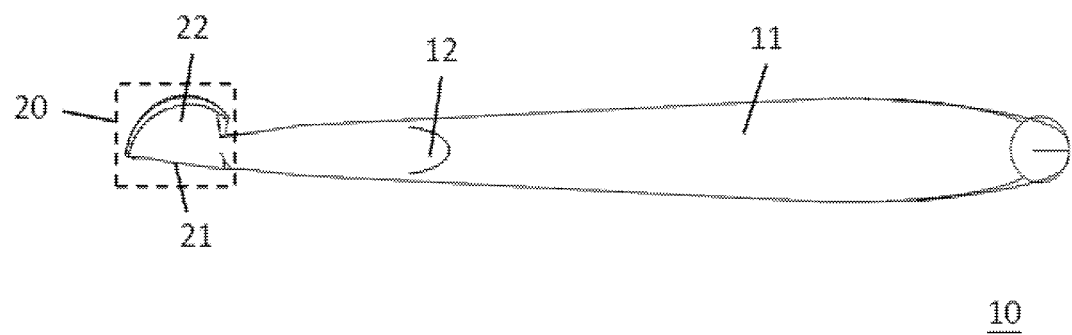
FIG. 2 is a side view of the contact lens tweezers in accordance with the first embodiment.

Following the first embodiment described above, refer to FIG. 2, a side view of the contact lens tweezers in accordance with the first embodiment is shown. The aforementioned contact lens tweezers 10 wherein the tip 20 comprises a bottom surface 21 and a convex structure 22, and the convex structure 22 is disposed on the bottom surface 21. The pair of legs 11 further comprising a holding portion 12 and the holding portion is for hand-held and force application.

Figure 3:
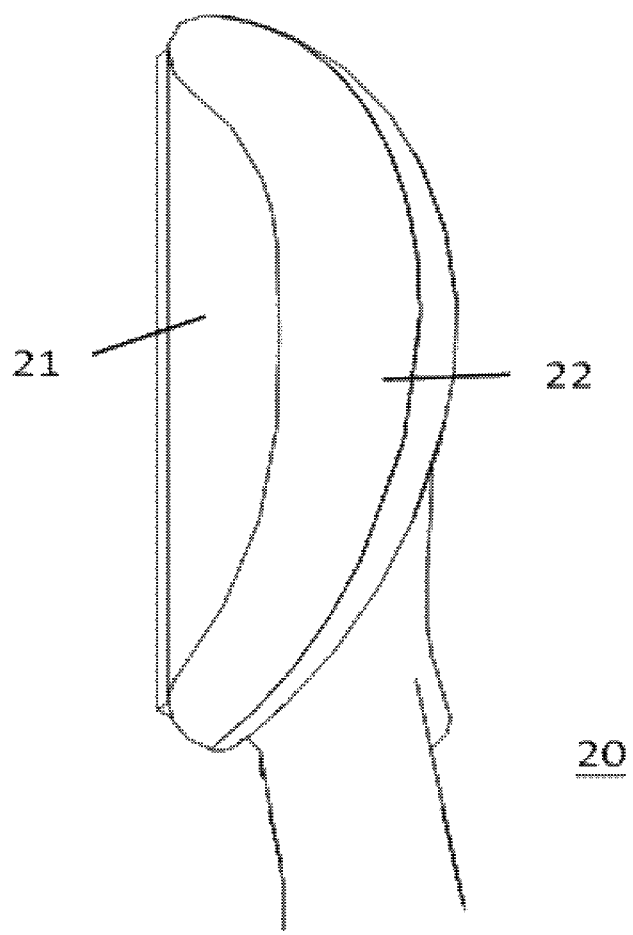
FIG. 3 is a top view of the tips of the contact lens tweezers in accordance with the first embodiment.

Following the first embodiment described above, refer to FIG. 3, a top view of the tips of the contact lens tweezers in accordance with the first embodiment. The aforementioned contact lens tweezers 10 wherein the tip 20 comprises a bottom surface 21 and a convex structure 22, the bottom surface is semicircular which support the contact lens. The appearance of the convex structure 22 is half-moon and user can use the convex structure 22 to attach the contact lens on eye to remove the contact lens, wherein the convex structure 22 increases the friction area between the tips and contact lens, so as to remove the contact lens according to the shape of eyeball. The material of the tip 20 is medical silicone gel.

Figure 4:
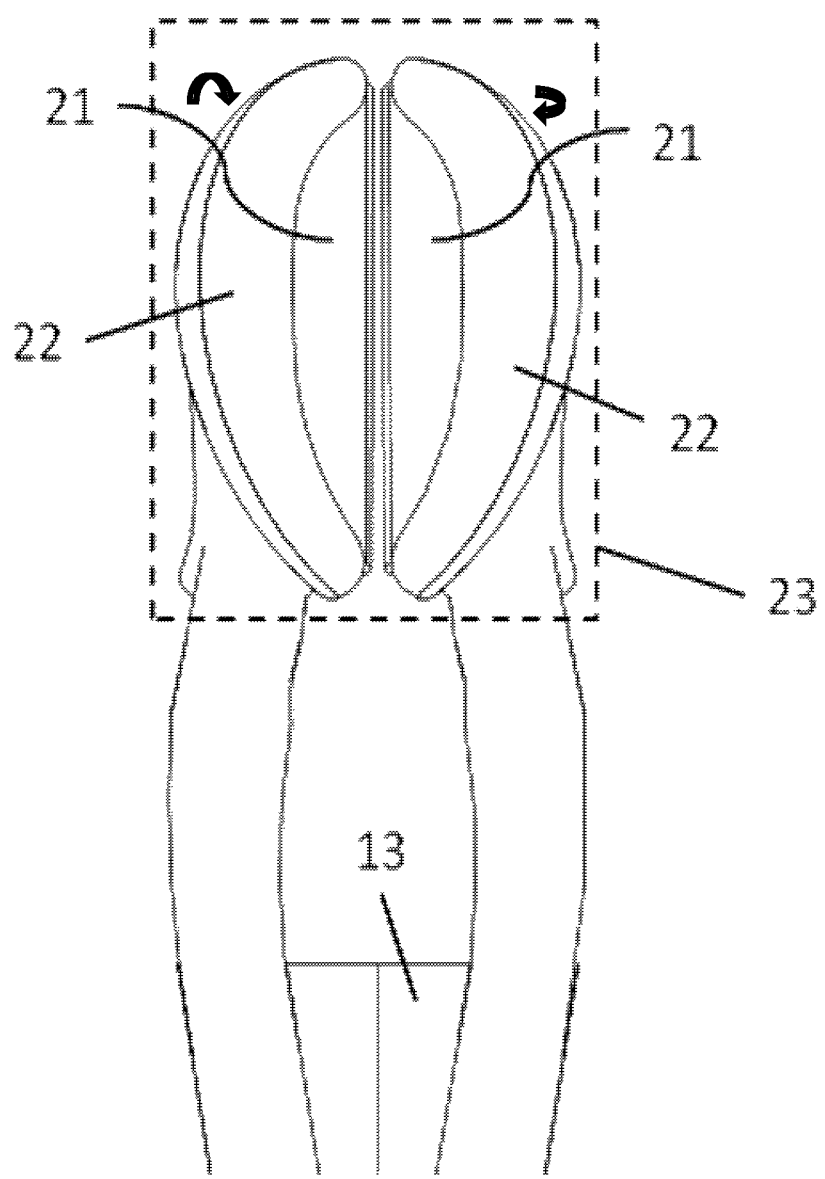
FIG. 4 is an enlarged top view of the contact lens tweezers in accordance with the first embodiment.

Following the first embodiment described above, refer to FIG. 4, an enlarged top view of the contact lens tweezers in accordance with the first embodiment. If the two tips 20 are pressed to close to each other, the bottom surface 21 and the convex structure 22 of the two tips 20 forming a curved structure 23, and the appearance of the curved structure 23 is a bowl-shape. Therefore, when user wants to wear the contact lens, it is easy to put the contact lens on the curved structure 23 which positioned with the curved surface facing downward and the concave surface facing upward. The curved structure 23 makes it easy to grip the contact lens or catch the contact lens, and attach the contact lens to eye. Furthermore, using the contact lens tweezers can prevent to scratch eye by finger or cause eye infections by bacteria which is on finger. Moreover, each leg of the pair of legs 11 further comprising a blocking lump 13 which in the middle of the leg. When the blocking lumps 13 of the pair of legs contact to each other, the two tips 20 rotate 60 degree like arrows indicate and forming a curved structure 23, and the blocking lumps 13 can prevent eye injury caused by the two staggered tips 20 due to user apply too much force during contact lens gripping or wearing.

Following the first embodiment described above, the material of the tip 20 can be further replaced with silicone gel, polyethylene (PE) or polyurethane (PU) The person skill in the art can choose suitable soft material for different purpose to modify the tips. The material of the pair of legs 11 can be replaced with rubber or metal. The pair of legs 11 of present invention has a U-shape appearance and the rotation angle of the tips is from 30 degree to 180 degree. The bottom surface 21 can be replaced with triangular, rectangular or polygonal; the appearance of the convex structure can be half-moon, and the curved structure 23 can be spoon-shaped or semicircular. The change and modification of above description do not limit any possible embodiments of the present invention.

Figure 5:
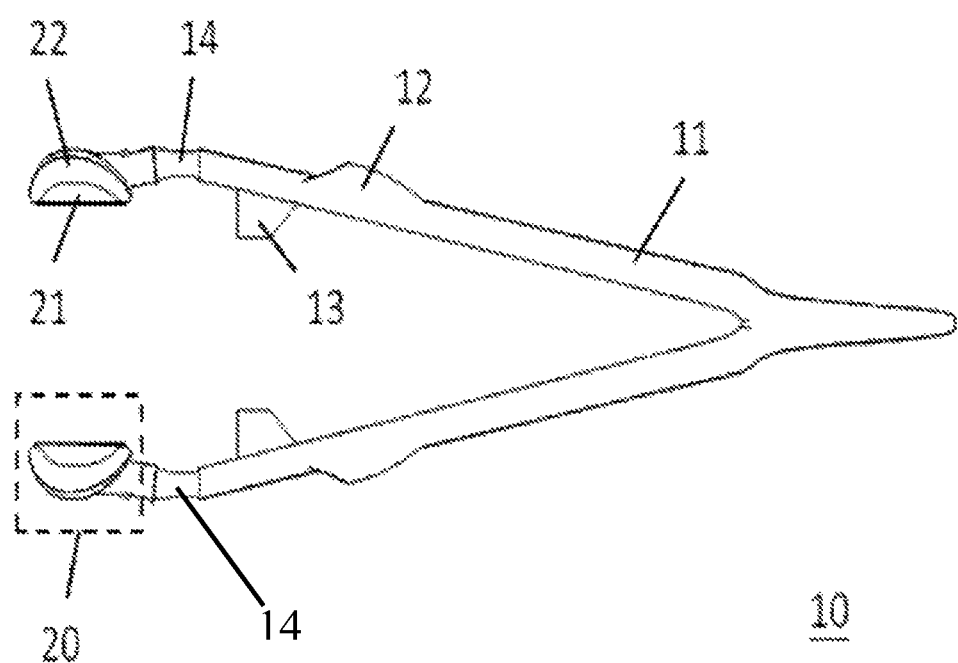
FIG. 5 is a top view of the contact lens tweezers in accordance with the second embodiment.
Figure 6:
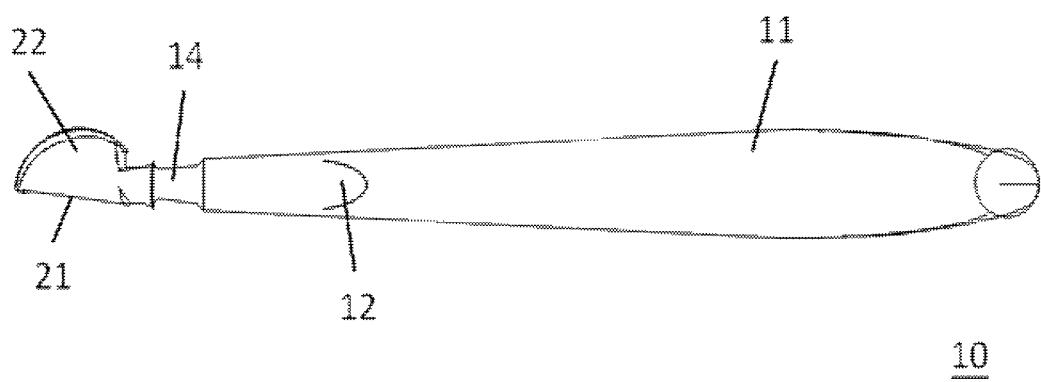
FIG. 6 is a side view of the contact lens tweezers in accordance with the second embodiment.

Referring to FIG. 5, a top view of the contact lens tweezers in accordance with the second embodiment. A contact lens tweezers 10 comprises tips 20, a pair of legs 11, holding portion 12, blocking lump 13 and two thin rods 14. The tips 20 are for gripping contact lens. The pair of legs 11 further comprising two thin rods 14, wherein each thin rod 14 connects with the tip 20 and the two thin rods 14 are flexible and bendable to enable the two tips 20 connect to each other. The pair of legs 11 has V-shape appearance. The material of the pair of legs 11 is flexible material like plastic and the pair of legs 11 is for hand holding and apply enforce to grip contact lens.

Following the second embodiment described above, a side view of the contact lens tweezers in accordance with the second embodiment. As aforementioned contact lens tweezers 10, wherein the tip 20 is at least formed by a bottom surface 21 and a convex structure 22, the convex structure 22 is disposed on the bottom surface 21. The pair of legs 11 further comprising two thin rods 14 which connect to the two tips 20 individually. The two thin rods 14 are made by plastic having flexibility and bendability, wherein the appearance of the thin rod is cylinder. Moreover, the leg of the pair of legs 11 further comprises a holding portion, which is for hand-held and apply force to grip the contact lens.

Following the second embodiment described above, please refer to FIG. 3, a top view of the tips of the contact lens tweezers in accordance with the first embodiment. As aforementioned contact lens tweezers 10, wherein the tip 20 is at least formed by a bottom surface 21 and a convex structure 22, the bottom surface 21 is semicircular structure to carry the contact lens. The appearance of the convex structure 22 is half-moon. User can use the convex structure 22 to attach the contact lens on eye. The convex structure 22 increase the friction area between the tips 20 and contact lens and it is easier to remove the contact lenses from eye according to the shape of the eye. And the material of the tip 20 is medical silicone gel.

Following the second embodiment described above, refer to FIG. 4, an enlarged top view of the contact lens tweezers in accordance with the first embodiment. If the two tips 20 are pressed to close to each other, the bottom surface 21 and the convex structure 22 of the two tips 20 combine to form a curved structure 23, and the curved structure 23 has bowl-shape appearance. Therefore, when user wants to wear the contact lens, it is easy to put the contact lens on the curved structure 23 which positioned with the curved surface facing downward and the concave surface facing upward. The curved structure 23 makes it easy to grip the contact lens or catch the contact lens, and attach the contact lens to eye. Furthermore, using the contact lens tweezers can prevent to scratch eye by finger or cause eye infections by bacteria which is on finger. Moreover, each leg of the pair of legs 11 further comprising a blocking lump 13 which in the middle of the leg. When the blocking lumps 13 of the pair of legs contact to each other, the two tips 20 rotate 30 degree like arrows indicate and forming a curved structure 23, and the blocking lumps 13 can prevent the two tips 20 to be staggered due to user apply too much force during contact lens gripping or wearing. So, the contact lens tweezers 10 can reduce eye injury.

Following the second embodiment described above, the material of the tips 20 of the contact lens tweezers 10 can be further replaced with silicone gel, polyethylene (PE) or polyurethane (PU) The person skill in the art can choose suitable soft material for different purpose to modify the tips. The material of the pair of legs 11 can be replaced with rubber or metal. The thin rods 14 is cuboid like, and an angle formed between the two thin rods 14 and the angle is between 15 and 60 degrees in this embodiments. The pair of legs 11 of present invention has a U-shape appearance and the rotation angle of the tips is from 30 degree to 180 degree. The bottom surface 21 can be replaced with triangular, rectangular or polygonal; the appearance of the convex structure can be half-moon, and the curved structure 23 can be spoon-shaped or semicircular. The change and modification of above description do not limit any possible embodiments of the present invention.

In summary, a contact lens tweezers of present invention with humanization Design to meet the actual demand. The contact lens tweezers solves existing shortcomings, and it shows obvious breakthrough advantage if compare to conventional technology. Therefore, the contact lens tweezers of present invention actually enhance the effect, function and performance, and it is not easy to achieve.

The foregoing detailed description is two possible embodiment of the present invention. They are not intended to be exhaustive or to limit the claim scope of the present invention. Many modifications and variations are possible in light of the above teaching. It is not intended to limit the scope of the disclosure, so it should be understood that other equivalents and modifications could be made thereto without departing from the spirit and scope of the disclosure.

What is claimed is:

1. A contact lens tweezers for wearing and removing a contact lens in position relative to an eye of a user, comprising:
   two tips for gripping the contact lens; and
   a pair of legs for hand holding which each leg connects with the tip and the legs connect to each other; wherein the tip comprises a bottom surface and a convex structure disposed on the bottom surface for increasing a friction area between the tips and the contact lens, wherein when the two tips press close to each other, the bottom surface and the convex structure forming a curved structure for gripping or wearing the contact lens, wherein each of the legs further comprises a blocking lump provided at the middle of the leg, when the blocking lumps of the legs contact to each other, the two tips are rotated at a rotation angle to form the curved structure.

2. The contact lens tweezers according to claim 1, wherein the contact lens tweezers further comprising two thin rods, wherein each thin rod connects with the tip and the two thin rods are flexible and bendable to enable the two tips to fit with the contact lens.

3. The contact lens tweezers according to claim 2, wherein when the two tips contact to each other, an angle formed between the two thin rods and the angle is between 15 and 90 degrees.

4. The contact lens tweezers according to claim 3, wherein the material of the two thin rods is flexible material.

5. The contact lens tweezers according to claim 2, wherein the leg of the pair of legs further comprising a holding portion.

6. The contact lens tweezers according to claim 2, wherein the rotation angle is between 30 and 180 degrees.

7. The contact lens tweezers according to claim 2, wherein the material of the tip is silicone gel, polyethylene or Polyurethane.

8. The contact lens tweezers according to claim 2, wherein the appearance of the convex structure is half-moon or semicircular.

9. The contact lens tweezers according to claim 2, wherein the material of the two thin rods is flexible material.

10. The contact lens tweezers according to claim 2, wherein the two thin rods is cylinder or cuboid.

11. The contact lens tweezers according to claim 2, wherein the shape of the pair of legs is V-shape.

12. The contact lens tweezers according to claim 1, wherein the leg of the pair of legs further comprising a holding portion, the holding portion is for hand-held and force application, wherein a shape of the curved structure is spoon-shaped, bowl-shaped or semicircular.

13. The contact lens tweezers according to claim 1, wherein the rotation angle is between 30 and 180 degrees.

14. The contact lens tweezers according to claim 1, wherein the material of the tip is silicone gel, polyethylene or Polyurethane.

15. The contact lens tweezers according to claim 1, wherein the appearance of the convex structure is half-moon or semicircular.

16. The contact lens tweezers according to claim 1, wherein the material of the pair of legs is flexible material.

17. The contact lens tweezers according to claim 1, wherein the shape of the pair of legs is V-shape.

* * * * *